United States Patent
Tang et al.

(10) Patent No.: US 6,365,371 B1
(45) Date of Patent: *Apr. 2, 2002

(54) CALCIUM BINDING PROTEIN

(75) Inventors: Y. Tom Tang, San Jose; Karl J. Guegler, Menlo Park; Neil C. Corley, Mountain View; Gina A. Gorgone, Boulder Creek, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/470,253

(22) Filed: Dec. 22, 1999

Related U.S. Application Data

(62) Division of application No. 09/190,965, filed on Nov. 13, 1998, now Pat. No. 6,071,721.
(51) Int. Cl.[7] .................... C12P 21/06; C07K 14/00
(52) U.S. Cl. .................. 435/69.1; 435/89.2; 435/6; 530/350; 530/23.1; 530/23.5; 514/12; 436/86
(58) Field of Search .................. 435/69.1, 6, 69.2; 530/350, 23.1, 23.5; 514/12; 436/86

(56) References Cited

PUBLICATIONS

Celio, M.R. et al., *Guidebook to the Calcium–Binding Proteins*, Oxford University Press, Oxford, UK. pp. 15–20 (1996).

Nozaki, M. et al., "Molecular Characterization of the Drosophila Mo25 Gene, Which is Conserved among Drosophila, Mouse, and Yeast", *DNA and Cell Biology* 15(6): 505–509 (1996).

Miyamoto, H. et al., "Molecular Cloning of a Novel mRNA Sequence Expressed in Cleavage Stage Mouse Embryos", *Mol. Reprod. Dev.* 34: 1–7 (1993).

Kissinger, C.R. et al., "Crystal structures of human calcineurin and the human FKBP12–FK506–calcineurin complex", *Nature* 378 (6557): 641–644 (1995).

Wang, M.G. et al., "Calcineurin A alpha (PPP3CA), calcineurin A beta (PPP3CB) and calcineurin B (PPP3R1) are located on human chromosomes 4, 10q21→q22 and 2p16→p15 respectively", *Cytogenet. Cell Genet.* 72: 236–241 (1996).

Rasmussen, C.D. and Means, A.R., "Calmodulin, cell growth and gene expression", *Trends in Neuroscience* 12: 433–438 (1989).

National Cancer Institute, Cancer Genome Anatomy Project (CGAP): "Homo sapiens cDNA cone similar MO25 protein" Emest Database Entry HS1182722, Accession No. AA278473, Apr. 3, 1997, XP002133736.

National Cancer Institute, Cancer Genome Anatomy Project (CGAP): "Homo sapiens cDNA cone similar to MO25 protein" Emest Database Entry HS1183536, Accession No. AA279145, Apr. 3, 1997, XP002133737.

*Primary Examiner*—Rebecca E. Prouty
*Assistant Examiner*—Richard Hutson
(74) *Attorney, Agent, or Firm*—IncyteGenomics, Inc.

(57) ABSTRACT

The invention provides a human calcium binding protein (hCBP) and polynucleotides which identify and encode hCBP. The invention also provides expression vectors, host cells, antibodies, agonists, and antagonists. The invention also provides methods for diagnosing, treating, or preventing disorders associated with expression of hCBP.

7 Claims, 6 Drawing Sheets

```
                                                   9                 18            27              36            45              54
                                              5' CAG AAA CAG AAC TGC CTG TGA CAG ATT AAG AGA CAA GCA AGG CTT GGA ATC TGA 63                72            81              90            99              108
                                              GAG CAA GCA AAG AGA GTG GAA ATT TAC AGC TGC CTT ATC ATT CCA TAT TGG AAG 117               126           135             144           153             162
                                              AAG AGA TTT CTA CAC ATG AAA AAA ATG CCT TTG TTT AGT AAA TCA CAC AAA AAT
                                                                        M   K   K   M   P   L   F   S   K   S   H   K   N 171               180           189             198           207             216
                                              CCA GCA GAA ATT GTG AAA ATC CTG AAA GAC AAT TTG GCC ATT TTG GAA AAG CAA
                                               P   A   E   I   V   K   I   L   K   D   N   L   A   I   L   E   K   Q 225               234           243             252           261             270
                                              GAC AAA AAG ACA GAC AAG GCT TCA GAA GAA GTG TCT AAA TCA CTG CAA GCA ATG
                                               D   K   K   T   D   K   A   S   E   E   V   S   K   S   L   Q   A   M 279               288           297             306           315             324
                                              AAA GAA ATT CTG TGT GGT ACA AAC GAG AAA GAA CCC ACA GAA GCA GTG GCT
                                               K   E   I   L   C   G   T   N   E   K   E   P   T   E   A   V   A 333               342           351             360           369             378
                                              CAG CTA GCA CAA GAA CTC TAC AGC AGT GGC CTG CTG GTG ACA CTG ATA GCT GAC
                                               Q   L   A   Q   E   L   Y   S   S   G   L   L   V   T   L   I   A   D

FIGURE 1A
```

```
        387           396           405           414           423           432
CTG CAG CTA ATA GAC TTT GAG GGA AAA AAA GAT GTG ACC CAG ATA TTT AAC AAC
 L   Q   L   I   D   F   E   G   K   K   D   V   T   Q   I   F   N   N 441           450           459           468           477           486
ATC TTG AGA AGA CAG GGC ATA ACT CGG AGT CCT ACT GTG GAG TAT ATT AGT GCT
 I   L   R   R   Q   G   I   T   R   S   P   T   V   E   Y   I   S   A 495           504           513           522           531           540
CAT CCT CAT ATC CTG TTT ATG CTC AAA GGA TAT GAA GCC CCA CAG ATT GCC
 H   P   H   I   L   F   M   L   K   G   Y   E   A   P   Q   I   A 549           558           567           576           585           594
TTA CGT TGT GGG ATT ATG CTG AGA GAA TGT ATT CGA CAT GAA CCA CTT GCC AAA
 L   R   C   G   I   M   L   R   E   C   I   R   H   E   P   L   A   K 603           612           621           630           639           648
ATC ATC TTT TCT AAT CAA TTC AGA GAT TTC AAG TAC GTG GAG TTG TCA
 I   I   L   F   S   N   Q   F   R   D   F   F   K   Y   V   E   L   S 657           666           675           684           693           702
ACA TTT GAT ATT GCT TCA GAT GCC TTT GCT ACT TTC AAG GAT TTA CTA ACC AGA
 T   F   D   I   A   S   D   A   F   A   T   F   K   D   L   L   T   R 711           720           729           738           747           756
CAT AAA GTG TTG GTA GCA GAC TTC TTA GAA CAA AAT TAC GAC ACT ATT TTT GAA
 H   K   V   L   V   A   D   F   L   E   Q   N   Y   D   T   I   F   E
```

FIGURE 1B

```
         765                774                783                792                801                810
GAC TAT GAG AAA TTG CTT CAG TCT GAG AAT TAT GTT ACT AAG AGA CAG TCT TTA
 D   Y   E   K   L   L   Q   S   E   N   Y   V   T   K   R   Q   S   L 819                828                837                846                855                864
AAG CTG CTA GGG GAG CTG ATC CTG GAC CGT CAC AAC TTT GCC ATC ATG ACA AAG
 K   L   L   G   E   L   I   L   D   R   H   N   F   A   I   M   T   K 873                882                891                900                909                918
TAT ATC AGC AAG CCG GAG AAC CTG AAA CTC ATG AAC CTC ATG CTT CGG GAT AAA
 Y   I   S   K   P   E   N   L   K   L   M   N   L   M   L   R   D   K 927                936                945                954                963                972
AGT CCC AAC ATC CAG TTT GAA GCC TTT CAT GTT TTT AAG GTG TTT GTG GCC AGT
 S   P   N   I   Q   F   E   A   F   H   V   F   K   V   F   V   A   S 981                990                999               1008               1017               1026
CCT CAC AAA ACA CAG CCT ATT GTG GAG ATC CTG TTA AAA AAT CAG CCC AAA CTC
 P   H   K   T   Q   P   I   V   E   I   L   L   K   N   Q   P   K   L 1035               1044               1053               1062               1071               1080
ATT GAG TTT CTG AGC AGC TTC CAA AAA GAA AGG ACG GAT GAT GAG CAG TTC GCT
 I   E   F   L   S   S   F   Q   K   E   R   T   D   D   E   Q   F   A 1089               1098               1107               1116               1125               1134
GAC GAG AAG AAC TAC TTG ATT AAA CAG ATC CGA GAC TTG AAG AAA ACG GCC CCT
 D   E   K   N   Y   L   I   K   Q   I   R   D   L   K   K   T   A   P
```

FIGURE 1C

```
1143           1152           1161           1170           1179           1188
TGA AGA GCT CCC CGG CCC CTG TCA CAG TCA GTC GTC TCA TTT GTC CAG TTT GTA 1197           1206           1215           1224           1233           1242
CAG TGT GTC ATT TCA GAA AGT CAT CAT TCT TGG GAA GAC TTT GGA GGT GCC TAT 1251           1260           1269           1278           1287           1296
TTT TTC TGC TGT AAT TGT TCT GGG TAG ATG GAG TAT AAA CAT TTG AAT GGA AAA 1305           1314           1323           1332           1341
AAA TTA ACC TAG AAT AAT ATA TTC ATT TTA GTC AAA AAA AAA AAA AAA   3'
```

FIGURE 1D

FIGURE 2A

| | | | | | | | | | | | | | | | | | | | | | | | | | |
|---|---|---|---|---|---|---|---|---|---|---|---|---|---|---|---|---|---|---|---|---|---|---|---|---|---|
| 1 | M | K | K | M | P | L | F | S | K | S | H | K | N | P | A | E | I | V | K | I | L | K | D | N | L | A | I | L | E | K | - | - | - | - | - | - | - | - | - | - | - | hCBP |
| 1 | M | P | - | F | P | - | F | G | K | S | H | K | S | P | A | D | L | V | K | N | L | K | E | S | M | A | V | L | E | K | - | - | - | - | - | - | - | - | - | - | - | g262934 |
| 1 | M | M | - | P | L | F | G | K | S | Q | K | S | P | V | E | L | V | K | S | L | K | E | A | I | N | A | L | E | A | - | - | - | - | - | - | - | - | - | - | g1794137 |
| 1 | M | P | L | - | - | L | F | G | K | S | H | K | S | P | A | D | V | K | T | L | R | E | V | T | I | L | D | K | L | P | P | P | K | L | D | K | D | G | g1255838 |

| 31 | Q | D | - | - | K | K | T | D | K | A | S | E | E | V | S | K | S | L | Q | A | M | K | E | I | L | C | G | T | N | E | K | E | P | P | T | E | - | A | V | hCBP |
| 29 | Q | D | - | I | S | D | K | K | A | E | K | A | T | E | E | V | S | K | K | N | L | V | A | M | K | E | I | L | Y | G | T | N | E | K | E | P | Q | T | E | - | A | V | g262934 |
| 28 | - | - | - | G | D | D | R | K | V | E | E | D | V | S | K | N | L | V | S | I | K | N | M | L | H | G | S | S | D | A | E | P | P | A | D | Y | V | V | g1794137 |
| 39 | N | I | Q | S | D | K | K | Y | D | K | A | L | D | E | V | S | K | N | V | A | M | I | K | S | F | I | Y | G | N | D | S | A | E | P | S | E | H | V | g1255838 |

| 67 | - | - | - | A | Q | L | A | Q | E | L | Y | S | S | G | L | L | V | T | L | I | A | D | L | Q | L | I | D | F | E | G | K | K | D | V | T | Q | I | F | N | N | I | hCBP |
| 68 | - | - | - | A | Q | L | A | Q | E | L | Y | N | S | G | L | L | G | T | L | V | A | D | L | Q | N | L | H | R | I | D | F | E | G | K | K | D | V | A | L | I | F | N | N | g262934 |
| 65 | - | - | - | A | Q | L | S | Q | E | L | Y | N | L | L | N | S | N | L | L | L | I | Q | N | L | H | I | K | F | E | E | C | K | K | D | H | V | G | Q | I | F | N | N | L | g1794137 |
| 79 | - | Q | V | A | Q | L | A | Q | E | V | Y | N | A | N | I | L | P | M | L | M | L | P | K | F | E | F | E | C | K | R | K | D | V | G | Q | I | F | N | N | L | g1255838 |

| 105 | L | R | R | Q | I | G | T | R | S | P | T | V | E | Y | I | S | A | H | P | H | I | L | F | M | L | L | K | G | Y | E | A | - | - | P | Q | I | A | L | R | C | hCBP |
| 106 | L | R | R | Q | I | G | T | R | T | P | T | V | E | Y | I | C | T | Q | Q | N | I | L | F | M | L | F | E | T | L | M | A | G | Y | E | S | - | - | P | E | I | A | L | N | C | g262934 |
| 103 | L | R | R | Q | I | G | T | R | S | P | T | V | E | Y | I | C | T | K | P | E | I | L | F | T | L | I | Q | L | V | Q | G | Y | - | - | S | V | P | D | I | A | L | T | C | g1794137 |
| 119 | L | G | A | R | P | E | Y | L | G | A | R | P | E | I | L | H | I | Q | L | V | Q | G | Y | - | - | S | V | P | D | H | A | L | T | C | g1255838 |

| 143 | G | I | M | L | R | E | C | I | R | H | E | P | L | A | K | I | I | L | F | S | N | Q | F | R | D | F | F | K | Y | V | E | L | S | T | F | D | I | A | S | D | hCBP |
| 144 | G | I | M | L | R | E | C | I | R | H | E | P | L | A | K | I | I | L | L | W | S | E | Q | F | Y | D | F | F | R | Y | V | E | M | S | T | F | D | I | A | S | D | g262934 |
| 143 | G | T | M | L | R | E | C | A | R | Y | E | A | L | A | K | I | M | H | I | H | S | D | E | F | F | K | F | F | R | Y | T | E | V | S | T | F | D | I | A | S | D | g1794137 |
| 157 | G | L | M | L | R | E | S | I | R | H | D | H | L | A | K | I | L | Y | S | D | V | F | Y | T | F | L | Y | V | Q | S | E | V | F | D | I | S | S | D | g1255838 |

```
183 A F A T F K D L L T R H K D L L V A D F L E Q N Y D T I F E D - Y E K L L Q S E N   hCBP
184 A F A T F K D L L T R H K L L L T E E F L E Q H Y D R F S E - Y E K L L H S E N   g262934
183 A F S T F K E L L T R H K L L S A E F L D A N Y D K F F S Q H Y Q R L L N S E N   g1794137
197 A F S T F K E L T T R H K A I H A E F L D S N Y D T F E A Q - Y Q N L L N S K N   g1255838

222 Y V T K R Q S L K L L G E L I L D R H N F A I M T K Y I S K P E N L K L M M N L   hCBP
223 Y V T K R Q S L K L L G E L L L D R H N F T I M T K Y I S K P E N L K L M M N L   g262934
223 Y V T R R Q S L K L L G E L L L D R H N F T V M T R Y I S E P E N L K L M M N M   g1794137
236 Y V T R R S L K L L G E L L L D R H N F N T M T K Y I S N P D N L R L M M E L    g1255838

262 L R D K S P N I Q F E E A F H V F K K V V A S P H K T Q P I V E I L L K N Q P K L   hCBP
263 L R D K S R N I Q F E E A F H V F K K V V A N P N K T Q P I H L D I L L K N Q T K L   g262934
263 L K E K S R N I Q F E E A F H V F K K V V A N P N K P Q P I H L D I L L R N Q T K L   g1794137
276 L R D K S R N I Q Y E A F H V F K K V V A N P N K P K P I S D I L L N R E K L      g1255838

302 I E F L S F Q K E R T D D E Q F A D E K N Y L I K Q I R D L K K T A - - - - -   hCBP
303 I E F L S K F Q N D R T E D D E Q Q F N D E K T Y L I K Q I R N L K R A A Q E - -   g262934
303 V D F L T N E F H T D D R T E D Q Q F N D E K A Y L I K Q I K E M K P L P - E - -   g1794137
316 V E F L S E E H H D R T D D E Q F A D E K T Y L I K Q I Q E M K S S P K E A K K   g1255838

337 - - - - - - - - - - - - - - - - P - -   hCBP
341 - - - - - - - - - - - - - - - - - A -   g262934
339 - - - - - - - - - - - - - - - - - A -   g1794137
356 P K S K E D E N Q E P A G P S E G P S T S Q   g1255838
```

FIGURE 2B

SEQUENCE LISTING

<160> NUMBER OF SEQ ID NOS: 5

<210> SEQ ID NO 1
<211> LENGTH: 337
<212> TYPE: PRT
<213> ORGANISM: Homo sapiens
<220> FEATURE: -
<223> OTHER INFORMATION: 3734805

<400> SEQUENCE: 1

```
Met Lys Lys Met Pro Leu Phe Ser Lys Ser His Lys Asn Pro Ala
 1               5                  10                  15

Glu Ile Val Lys Ile Leu Lys Asp Asn Leu Ala Ile Leu Glu Lys
                20                  25                  30

Gln Asp Lys Lys Thr Asp Lys Ala Ser Glu Glu Val Ser Lys Ser
                35                  40                  45

Leu Gln Ala Met Lys Glu Ile Leu Cys Gly Thr Asn Glu Lys Glu
                50                  55                  60

Pro Pro Thr Glu Ala Val Ala Gln Leu Ala Gln Glu Leu Tyr Ser
                65                  70                  75

Ser Gly Leu Leu Val Thr Leu Ile Ala Asp Leu Gln Leu Ile Asp
                80                  85                  90

Phe Glu Gly Lys Lys Asp Val Thr Gln Ile Phe Asn Asn Ile Leu
                95                  100                 105

Arg Arg Gln Ile Gly Thr Arg Ser Pro Thr Val Glu Tyr Ile Ser
                110                 115                 120

Ala His Pro His Ile Leu Phe Met Leu Leu Lys Gly Tyr Glu Ala
                125                 130                 135
```

```
Pro Gln Ile Ala Leu Arg Cys Gly Ile Met Leu Arg Glu Cys Ile
            140                 145                 150

Arg His Glu Pro Leu Ala Lys Ile Ile Leu Phe Ser Asn Gln Phe
            155                 160                 165

Arg Asp Phe Phe Lys Tyr Val Glu Leu Ser Thr Phe Asp Ile Ala
            170                 175                 180

Ser Asp Ala Phe Ala Thr Phe Lys Asp Leu Leu Thr Arg His Lys
            185                 190                 195

Val Leu Val Ala Asp Phe Leu Glu Gln Asn Tyr Asp Thr Ile Phe
            200                 205                 210

Glu Asp Tyr Glu Lys Leu Leu Gln Ser Glu Asn Tyr Val Thr Lys
            215                 220                 225

Arg Gln Ser Leu Lys Leu Leu Gly Glu Leu Ile Leu Asp Arg His
            230                 235                 240

Asn Phe Ala Ile Met Thr Lys Tyr Ile Ser Lys Pro Glu Asn Leu
            245                 250                 255

Lys Leu Met Met Asn Leu Leu Arg Asp Lys Ser Pro Asn Ile Gln
            260                 265                 270

Phe Glu Ala Phe His Val Phe Lys Val Phe Val Ala Ser Pro His
            275                 280                 285

Lys Thr Gln Pro Ile Val Glu Ile Leu Leu Lys Asn Gln Pro Lys
            290                 295                 300

Leu Ile Glu Phe Leu Ser Ser Phe Gln Lys Glu Arg Thr Asp Asp
            305                 310                 315

Glu Gln Phe Ala Asp Glu Lys Asn Tyr Leu Ile Lys Gln Ile Arg
            320                 325                 330

Asp Leu Lys Lys Thr Ala Pro
            335

<210> SEQ ID NO 2
<211> LENGTH: 1344
<212> TYPE: DNA
<213> ORGANISM: Homo sapiens
<220> FEATURE: -
<223> OTHER INFORMATION: 3734805

<400> SEQUENCE: 2
cagaaacaga actgcctgtg acagattaag agacaagcaa ggcttggaat ctgagagcaa      60
gcaaagagag tggaaattta cagctgcctt atcattccat attggaagaa gagatttcta     120
cacatgaaaa aaatgccttt gtttagtaaa tcacacaaaa atccagcaga aattgtgaaa     180
atcctgaaag acaatttggc cattttggaa agcaagaca aaaagacaga caaggcttca      240
gaagaagtgt ctaaatcact gcaagcaatg aaagaaattc tgtgtggtac aaacgagaaa     300 gaaccccga cagaagcagt ggctcagcta gcacaagaac tctacagcag tggcctgctg      360
gtgacactga tagctgacct gcagctgata gactttgagg gaaaaaaaga tgtgacccag     420
atatttaaca acatcttgag aagacagata ggcactcgga gtcctactgt ggagtatatt     480
agtgctcatc ctcatatcct gtttatgctc ctcaaaggat atgaagcccc acagattgcc     540
ttacgttgtg ggattatgct gagagaatgt attcgacatg aaccacttgc caaaatcatc     600 ctctttcta atcaattcag agatttcttt aagtacgtgg agttgtcaac atttgatatt     660
gcttcagatg cctttgctac tttcaaggat ttactaacca gacataaagt gttggtagca     720
gacttcttag aacaaaatta cgacactatt tttgaagact atgagaaatt gcttcagtct     780
gagaattatg ttactaagag acagtcttta aagctgctag gggagctgat cctggaccgt     840
```

-continued

```
cacaactttg ccatcatgac aaagtatatc agcaagccgg agaacctgaa actcatgatg      900
aacctccttc gggataaaag tcccaacatc cagtttgaag cctttcatgt ttttaaggtg      960
tttgtggcca gtcctcacaa aacacagcct attgtggaga tcctgttaaa aaatcagccc     1020
aaactcattg agtttctgag cagcttccaa aagaaagga cggatgatga gcagttcgct     1080
gacgagaaga actacttgat taaacagatc cgagacttga agaaaacggc cccttgaaga     1140
gctccccggc ccctgtcaca gtcagtcgtc tcatttgtcc agtttgtaca gtgtgtcatt     1200
tcagaaagtc atcattcttg ggaagacttt ggaggtgcct attttttctg ctgtaattgt     1260
tctgggtaga tggagtataa acatttgaat ggaaaaaaat taacctagaa taatatattc     1320
attttagtca aaaaaaaaaa aaaa                                             1344
```

<210> SEQ ID NO 3
<211> LENGTH: 341
<212> TYPE: PRT
<213> ORGANISM: Mus sp.
<220> FEATURE: -
<223> OTHER INFORMATION: g262934

<400> SEQUENCE: 3

```
Met Pro Phe Pro Phe Gly Lys Ser His Lys Ser Pro Ala Asp Ile
  1               5                  10                  15

Val Lys Asn Leu Lys Glu Ser Met Ala Val Leu Glu Lys Gln Asp
                 20                  25                  30

Ile Ser Asp Lys Lys Ala Glu Lys Ala Thr Glu Glu Val Ser Lys
                 35                  40                  45

Asn Leu Val Ala Met Lys Glu Ile Leu Tyr Gly Thr Asn Glu Lys
                 50                  55                  60

Glu Pro Gln Thr Glu Ala Val Ala Gln Leu Ala Gln Glu Leu Tyr
                 65                  70                  75

Asn Ser Gly Leu Leu Gly Thr Leu Val Ala Asp Leu Gln Leu Ile
                 80                  85                  90

Asp Phe Glu Gly Lys Lys Asp Val Ala Gln Ile Phe Asn Asn Ile
                 95                 100                 105

Leu Arg Arg Gln Ile Gly Thr Arg Thr Pro Thr Val Glu Tyr Ile
                110                 115                 120

Cys Thr Gln Gln Asn Ile Leu Phe Met Leu Leu Lys Gly Tyr Glu
                125                 130                 135

Ser Pro Glu Ile Ala Leu Asn Cys Gly Ile Met Leu Arg Glu Cys
                140                 145                 150

Ile Arg His Glu Pro Leu Ala Lys Ile Ile Leu Trp Ser Glu Gln
                155                 160                 165

Phe Tyr Asp Phe Arg Tyr Val Glu Met Ser Thr Phe Asp Ile
                170                 175                 180

Ala Ser Asp Ala Phe Ala Thr Phe Lys Asp Leu Leu Thr Arg His
                185                 190                 195

Lys Leu Leu Ser Ala Glu Phe Leu Glu Gln His Tyr Asp Arg Phe
                200                 205                 210

Phe Ser Glu Tyr Glu Lys Leu Leu His Ser Glu Asn Tyr Val Thr
                215                 220                 225

Lys Arg Gln Ser Leu Lys Leu Leu Gly Glu Leu Leu Leu Asp Arg
                230                 235                 240

His Asn Phe Thr Ile Met Thr Lys Tyr Ile Ser Lys Pro Glu Asn
                245                 250                 255
```

```
Leu Lys Leu Met Met Asn Leu Leu Arg Asp Lys Ser Arg Asn Ile
            260                 265                 270

Gln Phe Glu Ala Phe His Val Phe Lys Val Phe Val Ala Asn Pro
            275                 280                 285

Asn Lys Thr Gln Pro Ile Leu Asp Ile Leu Leu Lys Asn Gln Thr
            290                 295                 300

Lys Leu Ile Glu Phe Leu Ser Lys Phe Gln Asn Asp Arg Thr Glu
            305                 310                 315

Asp Glu Gln Phe Asn Asp Glu Lys Thr Tyr Leu Val Lys Gln Ile
            320                 325                 330

Arg Asn Leu Lys Arg Ala Ala Gln Gln Glu Ala
            335                 340

<210> SEQ ID NO 4
<211> LENGTH: 339
<212> TYPE: PRT
<213> ORGANISM: Drosophila melanogaster
<220> FEATURE: -
<223> OTHER INFORMATION: g1794137

<400> SEQUENCE: 4

Met Pro Leu Phe Gly Lys Ser Gln Lys Ser Pro Val Glu Leu Val
 1               5                  10                  15

Lys Ser Leu Lys Glu Ala Ile Asn Ala Leu Glu Ala Gly Asp Arg
            20                  25                  30

Lys Val Glu Lys Ala Gln Glu Asp Val Ser Lys Asn Leu Val Ser
            35                  40                  45

Ile Lys Asn Met Leu His Gly Ser Ser Asp Ala Glu Pro Pro Ala
            50                  55                  60

Asp Tyr Val Val Ala Gln Leu Ser Gln Glu Leu Tyr Asn Ser Asn
            65                  70                  75

Leu Leu Leu Leu Leu Ile Gln Asn Leu His Arg Ile Asp Phe Glu
            80                  85                  90

Gly Lys Lys His Val Ala Leu Ile Phe Asn Asn Leu Leu Arg Arg
            95                  100                 105

Gln Ile Gly Thr Arg Ser Pro Thr Val Glu Tyr Ile Cys Thr Lys
            110                 115                 120

Pro Glu Ile Leu Phe Thr Leu Met Ala Gly Tyr Glu Asp Ala His
            125                 130                 135

Pro Glu Ile Ala Leu Asn Ser Gly Thr Met Leu Arg Glu Cys Ala
            140                 145                 150

Arg Tyr Glu Ala Leu Ala Lys Ile Met Leu His Ser Asp Glu Phe
            155                 160                 165

Phe Lys Phe Phe Arg Tyr Val Glu Val Ser Thr Phe Asp Ile Ala
            170                 175                 180

Ser Asp Ala Phe Ser Thr Phe Lys Glu Leu Leu Thr Arg His Lys
            185                 190                 195

Leu Leu Cys Ala Glu Phe Leu Asp Ala Asn Tyr Asp Lys Phe Phe
            200                 205                 210

Ser Gln His Tyr Gln Arg Leu Leu Asn Ser Glu Asn Tyr Val Thr
            215                 220                 225

Arg Arg Gln Ser Leu Lys Leu Leu Gly Glu Leu Leu Leu Asp Arg
            230                 235                 240

His Asn Phe Thr Val Met Thr Arg Tyr Ile Ser Glu Pro Glu Asn
            245                 250                 255
```

```
Leu Lys Leu Met Met Asn Met Leu Lys Glu Lys Ser Arg Asn Ile
            260                 265                 270

Gln Phe Glu Ala Phe His Val Phe Lys Val Phe Val Ala Asn Pro
            275                 280                 285

Asn Lys Pro Lys Pro Ile Leu Asp Ile Leu Leu Arg Asn Gln Thr
            290                 295                 300

Lys Leu Val Asp Phe Leu Thr Asn Phe His Thr Asp Arg Ser Glu
            305                 310                 315

Asp Glu Gln Phe Asn Asp Glu Lys Ala Tyr Leu Ile Lys Gln Ile
            320                 325                 330

Lys Glu Leu Lys Pro Leu Pro Glu Ala
            335

<210> SEQ ID NO 5
<211> LENGTH: 377
<212> TYPE: PRT
<213> ORGANISM: Caenorhabditis elegans
<220> FEATURE: -
<223> OTHER INFORMATION: g1255838

<400> SEQUENCE: 5

Met Pro Leu Leu Phe Gly Lys Ser His Lys Ser Pro Ala Asp Val
  1               5                  10                  15

Val Lys Thr Leu Arg Glu Val Leu Thr Ile Leu Asp Lys Leu Pro
             20                  25                  30

Pro Pro Lys Leu Asp Lys Asp Gly Asn Ile Gln Ser Asp Lys Lys
             35                  40                  45

Tyr Asp Lys Ala Leu Asp Glu Val Ser Lys Asn Val Ala Met Ile
             50                  55                  60

Lys Ser Phe Ile Tyr Gly Asn Asp Ser Ala Glu Pro Ser Ser Glu
             65                  70                  75

His Val Val Gln Val Ala Gln Leu Ala Gln Glu Val Tyr Asn Ala
             80                  85                  90

Asn Ile Leu Pro Met Leu Ile Lys Met Leu Pro Lys Phe Glu Phe
             95                 100                 105

Glu Cys Lys Lys Asp Val Gly Gln Ile Phe Asn Asn Leu Leu Arg
            110                 115                 120

Arg Gln Ile Gly Thr Arg Ser Pro Thr Val Glu Tyr Leu Gly Ala
            125                 130                 135

Arg Pro Glu Ile Leu Ile Gln Leu Val Gln Gly Tyr Ser Val Pro
            140                 145                 150

Asp Ile Ala Leu Thr Cys Gly Leu Met Leu Arg Glu Ser Ile Arg
            155                 160                 165

His Asp His Leu Ala Lys Ile Ile Leu Tyr Ser Asp Val Phe Tyr
            170                 175                 180

Thr Phe Phe Leu Tyr Val Gln Ser Glu Val Phe Asp Ile Ser Ser
            185                 190                 195

Asp Ala Phe Ser Thr Phe Lys Glu Leu Thr Thr Arg His Lys Ala
            200                 205                 210

Ile Ile Ala Glu Phe Leu Asp Ser Asn Tyr Asp Thr Phe Phe Ala
            215                 220                 225

Gln Tyr Gln Asn Leu Leu Asn Ser Lys Asn Tyr Val Thr Arg Arg
            230                 235                 240

Gln Ser Leu Lys Leu Leu Gly Glu Leu Leu Asp Arg His Asn
            245                 250                 255
```

```
-continued

Phe Asn Thr Met Thr Lys Tyr Ile Ser Asn Pro Asp Asn Leu Arg
            260                 265                 270

Leu Met Met Glu Leu Leu Arg Asp Lys Ser Arg Asn Ile Gln Tyr
            275                 280                 285

Glu Ala Phe His Val Phe Lys Val Phe Val Ala Asn Pro Asn Lys
            290                 295                 300

Pro Lys Pro Ile Ser Asp Ile Leu Asn Arg Asn Arg Glu Lys Leu
            305                 310                 315

Val Glu Phe Leu Ser Glu Phe His Asn Asp Arg Thr Asp Asp Glu
            320                 325                 330

Gln Phe Asn Asp Glu Lys Ala Tyr Leu Ile Lys Gln Ile Gln Glu
            335                 340                 345

Met Lys Ser Ser Pro Lys Glu Ala Lys Lys Pro Lys Ser Lys Glu
            350                 355                 360

Asp Glu Asn Gln Glu Pro Ala Gly Pro Ser Glu Gly Pro Ser Thr
            365                 370                 375

Ser Gln
```

CALCIUM BINDING PROTEIN

This application is a divisional of U.S. Ser. No. 09/190,985 filed Nov. 13, 1998 now U.S. Pat. No. 6,071,721.

FIELD OF THE INVENTION

This invention relates to nucleic acid and amino acid sequences of a calcium binding protein and to the use of these sequences in the diagnosis, treatment, and prevention of cancer, reproductive disorders, immune disorders, and developmental disorders.

BACKGROUND OF THE INVENTION

In nearly all eukaryotic cells, calcium ($Ca^{2+}$) functions as an intracellular signaling molecule in diverse cellular processes including cell proliferation, neurotransmitter secretion, glycogen metabolism, and skeletal muscle contraction. Within a resting cell, the concentration of $Ca^{2+}$ in the cytosol is extremely low, $<10^{-7}$ M. However, when the cell is stimulated by an external signal, such as a neural impulse or a growth factor, the cytosolic concentration of $Ca^{2+}$ increases by about 50-fold. This influx of $Ca^{2+}$ is caused by the opening of plasma membrane $Ca^{2+}$ channels and the release of $Ca^{2+}$ from intracellular stores such as the endoplasmic reticulum. $Ca^{2+}$ directly activates regulatory enzymes, such as protein kinase C, which trigger signal transduction pathways. $Ca^{2+}$ also binds to specific $Ca^{2+}$-binding proteins (CBPs) such as calmodulin (CaM) which then activate multiple target proteins including enzymes, membrane transport pumps, and ion channels. CaM is the most widely distributed and the most common mediator of calcium effects and appears to be the primary sensor of $Ca^{2+}$ changes in eukaryotic cells. The binding of $Ca^{2+}$ to CaM induces marked conformational changes in the protein permitting interaction with, and regulation of over 100 different proteins. CaM interactions are involved in a multitude of cellular processes including but not limited to, gene regulation, DNA synthesis, cell cycle progression, mitosis, cytokinesis, cytoskeletal organization, muscle contraction, signal transduction, ion homeostasis, exocytosis, and metabolic regulation (Celio, M. R. et al. (1996) *Guidebook to Calcium-binding Protein*, Oxford University Press, Oxford, UK, pp. 15–20).

A novel mouse gene named MO25, expressed during early stages of development, has recently been identified and is believed to encode a CBP. The Drosophila equivalent of MO25, DMO25, encodes a polypeptide of 339 amino acid residues with a calculated molecular mass of 39.3 kDa. The novel CBP was found to be conserved among Drosophila, mouse, and yeast. In particular, the carboxy-terminal region of the protein is highly conserved among these species. A homology search revealed that the amino acid sequence of MO25 and DMO25 is similar to a protein encoded in an open reading frame near the calcineurin B subunit gene on chromosome XI in *Saccharomyces cerevisiae*. Calcineurin B is the small $Ca^{2+}$-binding regulatory subunit of calcineurin, a CaM-regulated protein phosphatase. The conservation of the MO25 and DMO25 gene structure among species and the wide tissue expression profile indicates that the function of the gene is likely to be fundamental in many cell types as well as during development (Nozaki, M. et al. (1996) DNA Cell Biol. 15:505–509; and Miyamoto, H. et al. (1993) Mol. Reprod. Dev. 34:1–7).

CBPs are implicated in a variety of disorders. For example, calcineurin is found in the cells of all eukaryotes ranging from yeast to mammals. Calcineurin is a target for inhibition by the immunosuppressive agents cyclosporin A and FK506 emphasizing its importance in immune disorders (Kissinger, C. R. et al. (1995) Nature 378:641–644). Calcineurin also plays a critical role in transcriptional regulation and growth control in T-lymphocytes (Wang, M. G. et al. (1996) Cytogenet. Cell Genet. 72:236–241). Additionally, levels of CaM are increased several-fold in tumors and tumor-derived cell lines for various types of cancer (Rasmussen, C. D. and Means, A. R. (1989) Trends in Neuroscience 12:433–438). Calcium binding S100β is another example of a CBP involved in a variety of disorders. S100β contains an EF-hand motif and is abundantly expressed in the nervous system. S100β levels are increased in the blood and cerebrospinal fluid of patients with neurological injury resulting from cerebral infarction, transient ischemic attacks, hemorrhagia, head trauma, and Down's syndrome. Furthermore, S100β and other neural-specific CBPs may also protect against neurodegenerative disorders, such as Alzheimer's, Parkinson's, and Huntington's diseases.

The discovery of a new calcium binding protein and the polynucleotides encoding it satisfies a need in the art by providing new compositions which are useful in the diagnosis, prevention, and treatment of cancer, reproductive disorders, immune disorders, and developmental disorders.

SUMMARY OF THE INVENTION

The invention is based on the discovery of a new human calcium binding protein. (hCBP), the polynucleotides encoding hCBP, and the use of these compositions for the diagnosis, treatment, or prevention of cancer, reproductive disorders, immune disorders, and developmental disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the amino acid sequence of SEQ ID NO:1 or a fragment of SEQ ID NO:1. The invention also includes an isolated and purified polynucleotide variant having at least 70% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide having a sequence which is complementary to the polynucleotide encoding the polypeptide comprising the amino acid sequence of SEQ ID NO:1 or a fragment of SEQ ID NO:1.

The invention also provides an isolated and purified polynucleo comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a disorder associated with decreased expression or activity of hCBP, the method comprising administering to a subject in need of such treatment an effective amount of a pharmaceutical composition comprising a substantially purified polypeptide having the amino acid sequence of SEQ ID NO:1 or a fragment of SEQ ID NO:1, in conjunction with a suitable pharmaceutical carrier.

The invention also provides a method for treating or preventing a disorder associated with increased expression or activity of hCBP, the method comprising administering to a subject in need of such treatment an effective amount of an antagonist of the polypeptide having the amino acid sequence of SEQ ID NO:1 or a fragment of SEQ ID NO:1.

BRIEF DESCRIPTION OF THE FIGURES AND TABLE

FIGS. 1A, 1B, 1C and 1D show the amino acid sequence (SEQ ID NO:1) and nucleic acid sequence (SEQ ID NO:2) of hCBP. The alignment was produced using MACDNASIS PRO software (Hitachi Software Engineering, South San Francisco, Calif.).

FIGS. 2A and 2B show the amino acid sequence alignment between hCBP (3734805; SEQ ID NO:1), MO25 (GI 262934; SEQ ID NO:3), DMO25 (GI 1794137; SEQ ID NO:4), and yeast-like CBP (GI 1255838; SEQ ID NO:5) produced using the multisequence alignment program of LASERGENE software (DNASTAR, Madison Wiss.).

Table 1 shows the programs, their descriptions, references, and threshold parameters used to analyze hCBP.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"hCBP" refers to the amino acid sequences of substantially purified hCBP obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to hCBP, increases or prolongs the duration of the effect of hCBP. Agonists may include proteins, nucleic acids, carbohydrates, or any other molecules which bind to modulate the effect of hCBP.

An "allelic variant" is an alternative form of the gene encoding hCBP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding hCBP include those sequences with deletions, insertions, or substitutions of different nucleotides, resulting in a polypeptide the same as hCBP or a polypeptide with at least one functional characteristic of hCBP. Included within this definition are polymorphisms which may or may not be readily detectable using a particular oligonucleotide probe of the polynucleotide encoding hCBP, and improper or unexpected hybridization to allelic variants, with a locus other than the normal chromosomal locus for the polynucleotide sequence encoding hCBP. The encoded protein may also be "altered," and may contain deletions, insertions, or substitutions of amino acid residues which produce a silent change and result in a functionally equivalent hCBP. Deliberate amino acid substitutions may be made on the basis of similarity in polarity, charge, solubility, hydrophobicity, hydrophilicity, and/or the amphipathic nature of the residues, as long as the biological or immunological activity of hCBP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of hCBP which are preferably at least 5 to about 15 amino acids in length, most preferably at least 14 amino acids, and which retain some biological activity or immunological activity of hCBP. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to hCBP, decreases the amount or the duration of the effect of the biological or immunological activity of hCBP. Antagonists may include proteins, nucleic acids, carbohydrates, antibodies, or any other molecule which decrease the effect of hCBP.

The term "antibody" refers to intact molecules as well as to fragments thereof, such as Fab, F(ab')$_2$, and Fv fragments, which are capable of binding the epitopic determinant. Antibodies that bind hCBP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic hCBP, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5'A-G-T 3'" bonds to the complementary sequence "3'T-C-A 5'". Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding hCBP or fragments of hCBP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GEL VIEW Fragment Assembly system (GCG, Madison Wiss.). Some sequences have been both extended and assembled to produce the consensus sequence.

The term "correlates with expression of a polynucleotide" indicates that the detection of the presence of nucleic acids, the same or related to a nucleic acid sequence encoding hCBP, by northern analysis is indicative of the presence of nucleic acids encoding hCBP in a sample, and thereby correlates with expression of the transcript from the polynucleotide encoding hCBP.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence on-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of hCBP. For example, modulation may cause an increase or a decrease in protein activity, binding characteristics, or any other biological, functional, or immunological properties of hCBP.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding hCBP, or fragments thereof, or hCBP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant of epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of hCBP polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to hCBP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of a new human calcium binding protein (hCBP), the polynucleotides encoding hCBP, and the use of these compositions for the diagnosis, treatment, or prevention of cancer, reproductive disorders, immune disorders, and developmental disorders.

Nucleic acids encoding the hCBP of the present invention were identified in Incyte Clone 3734805H1 from the coronary artery smooth muscle cDNA library (SMCCNOS01) using a computer search for nucleotide and/or amino acid sequence alignments. A consensus sequence, SEQ ID NO:2, was derived from the following overlapping and/or extended nucleic acid sequences: Incyte Clones 3734805H1 (SMCCNOS01), 3765972F6 (BRSTNOT24), 2260704X21C2 (UTRSNOT02), 2497543T6 (ADRETUT05), and shotgun sequence SBIA06584D1.

In one embodiment, the invention encompasses a polypeptide comprising the amino acid sequence of SEQ ID NO:1, as shown in FIGS. 1A, 1B, 1C and 1D. hCBP is 337 amino acids in length and has one potential cAMP- and cGMP-dependent protein kinase phosphorylation site at residue S228, five potential casein kinase II phosphorylation sites at residues S175, T186, T208, S250, and T313, and five potential protein kinase C phosphorylation sites at S10, T35, T186, T224, and S228. PRINTS analysis reveals a putative Huntingtin signature in hCBP within the region from about residues T224 through A243. The gene coding for Huntington, a protein associated with Huntington's disease contains a fragment that is unstable on Huntington's disease chromosomes. As shown in FIGS. 2A and 2B, hCBP has chemical and structural similarity with MO25 (GI 262934; SEQ ID NO:3), DMO25 (GI 1794137; SEQ ID NO:4), and yeast-like CBP (GI 1255838; SEQ ID NO:5). In particular, hCBP and MO25 share 80% identity, hCBP and DMO25 share 64% identity, and hCBP and yeast-like CBP share 60% identity. The Huntington signature found in hCBP is conserved in all three reference proteins, MO25, DMO25, and yeast-like CBP. In addition, the potential cAMP- and cGMP-dependent protein kinase phosphorylation site at residue S228, the potential casein kinase II phosphorylation sites at residues T186 and S250, and the potential protein kinase C phosphorylation sites at S10, T186, T224, and S228 of hCBP are conserved in MO25, DMO25, and yeast-like CBP. A fragment of SEQ ID NO:2 from about nucleotide 157 to about nucleotide 204 is useful in hybridization or amplification technologies to identify SEQ ID NO:2 and to distinguish between SEQ ID NO:2 and a related sequence. Northern analysis shows the expression of this sequence in various libraries, at least 44% of which are associated with cancer and at least 22% of which are associated with inflammation and the immune response. Of particular note is the expression of hCBP in reproductive tissue.

The invention also encompasses hCBP variants. A preferred hCBP variant is one which has at least about 80%, more preferably at least about 90%, and most preferably at least about 95% amino acid sequence identity to the hCBP amino acid sequence, and which contains at least one functional or structural characteristic of hCBP.

The invention also encompasses polynucleotides which encode hCBP. In a particular embodiment, the invention encompasses a polynucleotide sequence comprising the sequence of SEQ ID NO:2, which encodes hCBP.

The invention also encompasses a variant of a polynucleotide sequence encoding hCBP. In particular, such a variant polynucleotide sequence will have at least about 70%, more preferably at least about 85%, and most preferably at least about 95% polynucleotide sequence identity to the polynucleotide sequence encoding hCBP. A particular aspect of the invention encompasses a variant of SEQ ID NO:2 which has at least about 70% more preferably at least about 85%, and most preferably at least about 95% polynucleotide sequence identity to SEQ ID NO:2. Any one of the polynucleotide variants described above can encode an amino acid sequence which contains at least one functional or structural characteristic of hCBP.

It will be appreciated by those skilled in the art that as a result of the degeneracy of the genetic code, a multitude of polynucleotide sequences encoding hCBP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring hCBP, and all such variations are to be considered as being specifically disclosed.

Although nucleotide sequences which encode hCBP and its variants are preferably capable of hybridizing to the nucleotide sequence of the naturally occurring hCBP under appropriately selected conditions of stringency, it may be advantageous to produce nucleotide sequences encoding hCBP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding hCBP and its derivatives without altering the encoded amino acid sequences include the production of RNA transcripts having more desirable properties, such as a greater half-life, than transcripts produced from the naturally occurring sequence.

The invention also encompasses production of DNA sequences which encode hCBP and hCBP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding hCBP or any fragment thereof.

Also encompassed by the invention are polynucleotide sequences that are capable of hybridizing to the claimed polynucleotide sequences, and, in particular, to those shown in SEQ ID NO:2, or to a fragment of SEQ ID NO:2, under various conditions of stringency. (See, e.g., Wahl, G. M. and S. L. Berger (1987) Methods Enzymol. 152:399–407; Kimmel, A. R.(1987) Methods Enzymol. 152:507–511) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 pg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 $\mu$g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, was steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Robbins Hydra microdispenser (Robbins Scientific, Sunnyvale Calif.), Hamilton MICROLAB (Hamilton, Reno Nev.), Peltier Thermal Cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York, N.Y., unit 7.7; Meyers, R. A. (1995) *Molecular Biology and Biotechnology*, Wiley VCH, New York, N.Y., pp. 856–853.)

The nucleic acid sequences encoding hCBP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode hCBP may be cloned in recombinant DNA molecules that direct expression of hCBP, or fragments or functional equivalents thereof, in appropriate host cells. Due to the inherent degeneracy of the genetic code, other DNA sequences which encode substantially the same or a functionally equivalent amino acid sequence may be produced and used to express hCBP.

The nucleotide sequences of the present invention can be engineered using methods generally known in the art in order to alter hCBP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding hCBP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, hCBP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 43 IA peptide synthesizer (Perkin-Elmer). Additionally, the amino acid sequence of hCBP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins. Structures and Molecular Properties*, WH Freeman, New York, N.Y.)

In order to express a biologically active hCBP, the nucleotide sequences encoding hCBP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding hCBP. Such elements may vary in their strength and specificity. Specific initiation signals may also be used to achieve more efficient translation of sequences encoding hCBP. Such signals include the ATG initiation codon and adjacent sequences, e.g. the Kozak sequence. In cases where sequences encoding hCBP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probi. Cell Differ. 20:125–162.)

Methods which are well known to those skilled in the art may be used to construct expression vectors containing sequences encoding hCBP and appropriate transcriptional and translational control elements. These methods include in vitro recombinant DNA techniques, synthetic techniques, and in vivo genetic recombination. (See, e.g., Sambrook, J. et al. (1989) *Molecular Cloning A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York, N.Y., ch. 9, 13, and 16.)

A variety of expression vector/host systems may be utilized to contain and express sequences encoding hCBP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding hCBP. For example, routine cloning, subcloning, and propagation of polynucleotide sequences encoding hCBP can be achieved using a multifunctional *E. coli* vector such as PBLUESCRIPT (Stratagene, La Jolla Calif.) or pSPORT plasmid (Life Technologies,. Ligation of sequences encoding hCBP into the vector's multiple cloning site disrupts the lacZ gene, allowing a calorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of hCBP are needed, e.g. for the production of antibodies, vectors which direct high level expression of hCBP may be used. For example, vectors containing the strong, inducible T5 or T7 bacteriophage promoter may be used.

Yeast expression systems may be used for production of hCBP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995; supra; Grant et al. (1987) Methods Enzymol. 153:516–54; and Scorer, C. A. et al. (1994) Bio/Technology 12:181–184.)

Plant systems may also be used for expression of hCBP. Transcription of sequences encoding hCBP may be driven by viral promoters, e.g, the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York, N.Y., pp. 191–196.)

In mammalian cells, a number of viral-based expression systems may be utilized. In cases where an adenovirus is used as an expression vector, sequences encoding hCBP may be ligated into an adenovirus transcription/translation complex consisting of the late promoter and tripartite leader sequence. Insertion in a non-essential E1 or E3 region of the viral genome may be used to obtain infective virus which expresses hCBP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of hCBP in cell lines is preferred. For example, sequences encoding hCBP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ or $apr^-$ cells, respectively. (See, e.g., Wigler, M. et al. (1977) Cell 11:223–232; Lowy, I. et al; (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartnan, S. C. and R. C. Mulligan (1988) Proc. Natl. Acad. Sci. 85:8047–8051.) Visible markers, e.g., anthocyanins, green fluorescent proteins (GFP; Clontech), B glucuronidase and its substrate β glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding hCBP is inserted within a marker gene sequence, transformed cells containing sequences encoding hCBP can be identified by the absence of marker gene function. Alternatively, a marker gene can be placed in tandem with a sequence encoding hCBP under the control of a single promoter. Expression of the marker gene in response to induction or selection usually indicates expression of the tandem gene as well.

In general, host cells that contain the nucleic acid sequence encoding hCBP and that express hCBP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of hCBP using either specific polyclonal or monoclonal antibodies are known in the art. Examples of such Techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on hCBP is preferred, but a competitive binding assay may be employed. These and other assays are well known in the art. (See, e.g., Hampton, R. et al. (1990) *Serological Methods. a Laboratory Manual*, APS Press, St Paul Minn., Sect. IV; Coligan, J. E. et al. (1997) *Current Protocols in Immunology*, Greene Pub. Associates and Wiley-Interscience, New York, N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding hCBP include oligolabeling, nick translation, end-labeling, or PCR amplification using a labeled nucleotide. Alternatively, the sequences encoding hCBP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wiss.), and US Biochemical Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding hCBP may be cultured under conditions suitable for the expression and recovery of the protein from cell culture, The protein produced by a transformed cell may be secreted or retained intracellularly depending on the sequence and/or the vector used. As will be understood by those of skill in the art, expression vectors containing polynucleotides which encode hCBP may be designed to contain signal sequences which direct secretion of hCBP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda M.d.) and may be chosen to ensure the correct modification and processing of the foreign protein.

In another embodiment of the invention, natural, modified, or recombinant nucleic acid sequences encoding hCBP may be ligated to a heterologous sequence resulting in translation of a fusion protein in any of the aforementioned host systems. For example, a chimeric hCBP protein containing a heterologous moiety that can be recognized by a commercially available antibody may facilitate the screening of peptide libraries for inhibitors of hCBP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the hCBP encoding sequence and the heterologous protein sequence, so that hCBP may be cleaved away from the heterologous moiety following purification. Methods for fusion protein expression and purification are discussed in Ausubel (1995, supra ch 10). A variety of commercially available kits may also be used to facilitate expression and purification of fusion proteins.

In a further embodiment of the invention, synthesis of radiolabeled hCBP may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of hCBP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved; for example, using the ABI 431A Peptide Synthesizer (Perkin-Elmer). Various fragments of hCBP may be synthesized separately and then combined to produce the full length molecule.

THERAPEUTICS

Chemical and structural similarity, e.g., in the context of sequences and motifs, exists between regions of hCBP, MO25 (GI 262934), DMO25 (GI 1794137), and yeast-like CBP (GI 1255838). In addition, the expression of hCBP is closely associated with cancer, reproductive tissues, inflammation and the immune response. Therefore, hCBP appears to play a role in cancer, reproductive disorders, immune disorders, and developmental disorders. In the treatment of cancer, reproductive disorders, immune disorders, and developmental disorders associated with increased hCBP expression or activity, it is desirable to decrease the expression or activity of hCBP. In the treatment of the above conditions associated with decreased hCBP expression or activity, it is desirable to increase the expression or activity of hCBP.

Therefore, in one embodiment, hCBP or a fragment or derivative thereof may be administered to a subject to treat or prevent a disorder associated with decreased expression or activity of hCBP. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart., kidney, liver, lung, muscle, ovary, pancreas, parathyroid, penis, prostate, salivary glands, skin, spleen, testis, thymus, thyroid, and uterus; a reproductive disorder such as disorders of prolactin production, infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis, cancer of the breast, fibrocystic breast disease, and galactorrhea, disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia; a developmental disorder, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; and an immune disorder, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dernatitis, Crohn's disease, atopic dennatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scieroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing hCBP or a fragment or derivative thereof may be administered to a subject to treat or prevent a disorder associated with decreased expression or activity of hCBP including, but not limited to, those described above.

In a further embodiment, a pharmaceutical composition comprising a substantially purified hCBP in conjunction with a suitable pharmaceutical carrier may be administered to a subject to treat or prevent a disorder associated with decreased expression or activity of hCBP including, but not limited to, those provided above.

In still another embodiment, an agonist which modulates the activity of hCBP may be administered to a subject to treat or prevent a disorder associated with decreased expression or activity of hCBP including, but not limited to, those listed above.

In a further embodiment, an antagonist of hCBP may be administered to a subject to treat or prevent a disorder associated with increased expression or activity of hCBP. Such disorders may include, but are not limited to, those discussed above. In one aspect, an antibody which specifically binds hCBP may be used directly as an antagonist or indirectly as a targeting or delivery mechanism for bringing a pharmaceutical agent to cells or tissue which express hCBP.

In an additional embodiment, a vector expressing the complement of the polynucleotide encoding hCBP may be administered to a subject to treat or prevent a disorder associated with increased expression or activity of hCBP including, but not limited to, those described above.

In other embodiments, any of the proteins, antagonists, antibodies, agonists, complementary sequenices, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of hCBP may be produced using methods which are generally known in the art. In particular, purified hCBP may be used to produce antibodies or to screen libraries of pharmaceutical agents to identify those which specifically bind hCBP. Antibodies to hCBP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with hCBP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to hCBP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of hCBP amino acids may be fused with those of another protein, such as KLH, and antibodies to the chimeric molecule may be produced.

Monoclonal antibodies to hCBP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbot, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce hCBP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for hCBP may also be generated. For example, such fragments include; but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between hCBP and its specific antibody. A two-site, monoclonal-based immunoassay utilizing monoclonal antibodies reactive to two non-interfering hCBP epitopes is preferred, but a competitive binding assay may also be employed (Pound, sura).

Various methods such as Scatchard analysis in conjunction with radioimmunoassay techniques may be used to assess the affinity of antibodies for hCBP. Affinity is expressed as an association constant, $K_a$, which is defined as the molar concentration of hCBP-antibody complex divided by the molar concentrations of free antigen and free antibody under equilibrium conditions. The $K_a$ determined for a preparation of polyclonal antibodies, which are heterogeneous in their affinities for multiple hCBP epitopes, represents the average affinity, or avidity, of the antibodies for hCBP. The $K_a$ determined for a preparation of monoclonal antibodies, which are monospecific for a particular hCBP epitope, represents a true measure of affinity. High-affinity antibody preparations with. $K_a$ ranging from about $10^9$ to $10^{12}$ 1/mole are preferred for use in immunoassays in which the hCBP-antibody complex must withstand rigorous manipulations. Low-affinity antibody preparations with $K_a$ ranging from about $10^6$ to $10^7$l/mole are preferred for use in immunopurification and similar procedures which ultimately require dissociation of hCBP, preferably in active form, from the antibody (Catty, D. (1988) Antibodies. Volume I: A Practical Approach, IRL Press, Washington D.C.; Liddell, J. E. and Cryer, A. (1991) A Practical Guide to Monoclonal Antibodies, John Wiley & Sons, New York, N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of hCBP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding hCBP, or any fragment or complement thereof, may be used for therapeutic purposes. In one aspect, the complement of the polynucleotide encoding hCBP may be used in situations in which it would be desirable to block the transcription of the MRNA. In particular, cells may be transformed with sequences complementary to polynucleotides encoding hCBP. Thus, complementary molecules or fragments may be used to modulate hCBP activity, or to achieve regulation of gene function. Such technology is now well known in the art, and sense or antisense oligonucleotides or larger fragments can be designed from various locations along the coding or control regions of sequences encoding hCBP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding hCBP. (See, e.g., Sambrook, supra; Ausubel, 1995, supra.)

Genes encoding hCBP can be turned off by transforming a cell or tissue with expression vectors which express high levels of a polynucleotide, or fragment thereof, encoding hCBP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding hCBP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules.

Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding hCBP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding hCBP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of hCBP, antibodies to hCBP, and mimetics, agonists, antagonists, or inhibitors of hCBP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of hCBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example hCBP or fragments thereof, antibodies of hCBP, and agonists, antagonists or inhibitors of hCBP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in. 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind hCBP may be used for the diagnosis of disorders characterized by expression of hCBP, or in assays to monitor patients being treated with hCBP or agonists, antagonists, or inhibitors of hCBP. Antibodies useful for diagnostic purposes may be prepared in the same manner as described above for therapeutics. Diagnostic assays for hCBP include methods which utilize the antibody and a label to detect hCBP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring hCBP, including ELISAs, RIAs, and FACS, are known in the art and provide a basis for diagnosing altered or abnormal levels of hCBP expression. Normal or standard values for hCBP expression are established by combining body fluids or cell extracts taken from normal mammalian subjects, preferably human, with antibody to hCBP. under conditions suitable for complex formation. The amount of standard complex formation may be quantitated by various methods, preferably by photometric means. Quantities of hCBP expressed in subject, control, and disease samples from biopsied tissues are compared with the standard values. Deviation between standard and subject values establishes the parameters for diagnosing disease.

In another embodiment of the invention, the polynucleotides encoding hCBP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of hCBP may be correlated with disease. The diagnostic assay may be used to determine absence, presence, and excess expression of hCBP, and to monitor regulation of hCBP levels during therapeutic intervention.

In one aspect, hybridization with PCR probes which are capable of detecting polynucleotide sequences, including genomic sequences, encoding hCBP or closely related molecules may be used to identify nucleic acid sequences which encode hCBP. The specificity of the probe, whether it is made from a highly specific region, e.g.,. the 5' regulatory region, or from a less specific region, e.g., a conserved motif, and the stringency of the hybridization or amplification (maximal, high, intermediate, or low), will determine whether the probe identifies only naturally occurring sequences encoding hCBP, allelic variants, or related sequences.

Probes may also be used for the detection of related sequences, and should preferably have at least 50% sequence identity to any of the hCBP encoding sequences. The hybridization probes of the subject invention may be DNA or RNA and may be derived from the sequence of SEQ ID NO:2 or from genomic sequences including promoters, enhancers, and introns of the hCBP gene.

Means for producing specific hybridization probes for DNAs encoding hCBP include the cloning of polynucleotide sequences encoding hCBP or hCBP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding hCBP may be used for the diagnosis of disorders associated with expression of hCBP. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a reproductive disorder such as disorders of prolactin production, infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis, cancer of the breast, fibrocystic breast disease, and galactorrhea, disruptions of spermatogenesis, abnormal sperm physiology, cancer of the testis, cancer of the prostate, benign prostatic hyperplasia,. prostatitis, Peyronie's disease, impotence, carcinoma of the male breast, and gynecomastia; a developmental disorder, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myclodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; and an immune disorder, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetal is, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding hCBP may be used in Southern or northern analysis, dot blot, or other membrane-based technologies; in PCR technologies; in dipstick, pin, and multiformat ELISA-like assays; and in microarrays utilizing fluids or tissues from patients to detect altered hCBP expression. Such qualitative or quantitative methods are well known in the art.

In a particular aspect, the nucleotide sequences encoding hCBP may be useful in assays that detect the presence of associated disorders, particularly those mentioned above. The nucleotide sequences encoding hCBP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding hCBP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of hCBP, a normal or standard profile for expression is established. This may be accomplished by combining body fluids or cell extracts taken from normal subjects, either animal or human, with a sequence, or a fragment thereof, encoding hCBP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or over-expressed) in biopsied tissue from an individual may indicate a predisposition for the development of the: disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding hCBP may involve the use of PCR. These oligomers may be chemically synthesized, generated enzymatically, or produced in vitro. Oligomers will preferably contain a fragment of a polynucleotide encoding hCBP, or a fragment of a polynucleotide complementary to the polynucleotide encoding hCBP, and will be employed under optimized conditions for identification of a specific gene or condition. Oligomers may also be employed under less stringent conditions for detection or quantitation of closely related DNA or RNA sequences.

Methods which may also be used to quantitate the expression of hCBP include radiolabeling or biotinylating nucleotides, coamplification of a control nucleic acid, and interpolating results from standari curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Nat. Acad. Sci. 94:2150–2155; and Heller, M. J. et al. (1997) U.S. Pat. No. 5,605,662.)

In another embodiment of the invention, nucleic acid sequences encoding hCBP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding hCBP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or-arm-of a particular human chromosome is not known. New sequences can be assigned to chromosomal arms by physical mapping, This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, hCBP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between hCBP and the agent being tested may be measured.

Another technique for drug screening provides for high throughput screening of compounds having suitable binding affinity to the protein of interest. (See, e.g., Geysen, et al. (1984) PCT application WO84/103564.) In this method, large numbers of different small test compounds are synthesized on a solid substrate. The test compounds are reacted with hCBP, or fragments thereof, and washed. Bound hCBP is then detected by methods well known in the art. Purified hCBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding hCBP specifically compete with a test compound for binding hCBP. In this manner, antibodies can be used to detect the presence of any peptide which shares one or more antigenic determinants with hCBP.

In additional embodiments, the nucleotide sequences which encode hCBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. SMCCNOS01 cDNA Library Construction

The SMCCNOS01 subtracted coronary artery smooth muscle cell library was constructed using $7.56 \times 10^6$ clones from the SMCCNOT02 library and was subjected to two rounds of subtraction hybridization for 48 hours with $6.12 \times 10^6$ clones from SMCCNOTO1. The starting library for subtraction was constructed using RNA isolated from coronary artery smooth muscle cells removed from a 3-year-old Caucasian male. The cells were treated with TNFα and IL-1β 10 ng/ml each for 20 hours. The hybridization probe for subtraction was derived from a similarly constructed library from RNA isolated from untreated coronary artery smooth muscle cells from the same donor. Subtractive hybridization conditions were based on the methodologies of Swaroop et al. NAR (1991) 19:1954, and Bonaldo et al. Genome Research (1996) 6:791.

For both cDNA libraries SMCCNOTO1 and SMCCNOT02, the frozen coronary artery smooth muscle cells (50–100 mg) were homogenized in GTC homogenization buffer (4.0M guanidine thiocyanate, 0.1M Tris-HCl pH 7.5, 1%2-Mercaptoethanol). Two volumes of binding buffer (0.4M LiCl, 0.1M Tris-HCl pH 7.5, 0.02M EDTA) were added and the resulting mixture vortexed at 13,000 rpm. The supernatant was removed and combined with Oligo(dT)$_{25}$ bound MPG Streptavidin particles. After rotation at room temperature, the mRNA-Oligo(dT)$_{25}$-Streptavidin particles were separated from the supernatant, washed twice with hybridization buffer I (0.15M NaCl, 0.01M Tris-HCl pH8.0, 1 mM EDTA, 0.1% Lauryl Sarcosinate) and washed twice with hybridization buffer II (0.15M NaCl, 0.01M Tris-HCl pH8.0, 1 mM EDTA) using magnetic separation at each step to remove the supernatant from the particles. Bound mRNA was eluted from the MPG Streptavidin particles with release solution and heated to 65° C. The supernatant containing eluted mRNA was magnetically separated from the Streptavidin particles and used to construct the cDNA libraries.

Poly(A+) RNA was used for cDNA synthesis and construction of the cDNA library according to the recommended protocols in the SUPERSCRIPT plasmid system (Life Technologies). The cDNAs were fractionated on a SEPHAROSE CL4B column (Amersham Pharmacia Biotech), and those cDNAs exceeding 400 bp were ligated into pINCY (Incyte Pharmaceuticals, Palo Alto, Calif.). Recombinant plasmids were transformed into DH5α competent cells or ElectroMAX® cells (Life Technologies).

II. Isolation of CDNA Clones

Plasmid DNA was released from the cells and purified using the REAL Prep 96 plasmid kit (QIAGEN). The recommended protocol was employed except for the following changes: 1) the bacteria were cultured in 1 ml of sterile Terrific Broth (Life Technologies) with carbenicillin at 25 mg/l and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4 ° C.

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 summarizes the software programs, descriptions, references, and threshold parameters used. The first column of Table 1 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering) and LASER-GENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probalislitic approach which analyzes consensus primary structures of gene families. (See, e.g., Eddy, S. R. (1996) Cur. Opin. Str. Biol. 6:361–365.)

The programs described above for the assembly and analysis of full length polynucleotide and amino acid sequences were used to identify polynucleotide sequence fragments from SEQ ID NO:2. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals, Palo Alto Calif.). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \text{maximum } BLAST \text{ score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding hCBP occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in the description of the invention.

V. Extension of hCBP Encoding Polynucleotides

The full length nucleic acid sequence of SEQ ID NO:2 was produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharnacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4:68° C., 2 min; Step 5: Steps 2, 3, and 4 repeated 20 times; Step 6: 68° C., 5 min; Step 7: storage at 4° C. parameters for primer pair T7 and SK+ were as follows: Step 1: 94° C., 3 min; Step 2: 94° C., 15 sec; Step 2:94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICO GREEN quantitation reagent (0.25% (v/v) PICO GREEN; Molecular Probes, Eugene Oreg.) dissolved in 1X TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wiss.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: step 2, 3, and repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequence of SEQ ID NO:2 is used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [$^{32}$P]-adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the hCBP-encoding sequences, or any parts thereof, are used to detect, decrease, or inhibit expression of naturally occurring hCBP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of hCBP. To. inhibit transcription, a complementary oligonucleotide is designed from the most unique 5' sequence and used to prevent promoter binding to the coding sequence. To inhibit translation, a complementary oligonucleotide is designed to prevent ribosomal binding to the hCBP-encoding transcript.

IX. Expression of hCBP

Expression and purification of hCBP are achieved using bacterial or virus-based expression systems. For expression of hCBP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express hCBP upon induction with isopropyl beta-D-thiogalactopyranoside (IPTG). Expression of hCBP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding hCBP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, hCBP is synthesized as a fusion protein with, e.g., glutathione S-transferase (GST) or a peptide epitope tag, such as FLAG or 6-His, permitting rapid, single-step, affiniiy-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from hCBP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified hCBP obtained by these methods can be used directly in the following activity assay.

X. Demonstration of HCBP Activity

The assay for human calcium-binding proteins is based upon the ability of hCBPs to down-regulate mitosis. hCBP can be expressed by transforming a mammalian cell line such as COS7, HeLa or CHO with an eukaryotic expression vector encoding hCBP. Eukaryotic expression vectors are commercially available, and the techniques to introduce them into cells are well known to those skilled in the art. The cells are incubated for 48–72 hours after transformation under conditions appropriate for the cell line to allow expression of hCBP. Then, phase microscopy is used to compare the mitotic index of transformed versus control cells. The decrease in the mitotic index is proportional to the hCBP activity.

XI. Functional Assays hCBP function is assessed by expressing the sequences encoding hCBP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate cellular properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York, N.Y.

The influence of hCBP on gene expression can be assessed using highly purified populations of cells transfected with sequences encoding hCBP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding hCBP and other genes of interest can be analyzed by northern analysis or microarray techniques.

XII. Production of hCBP Specific Antibodies hCBP substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the hCBP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431 A Peptide Synthesizer (Perkin-Elmer) using fmoc-chemistry and coupled to KLH (Sigma-Aldrich, St. Louis Mo. by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring hCBP Using Specific Antibodies

Naturally occurring or recombinant hCBP is substantially purified by immunoaffinity chromatography using antibodies specific for hCBP. An immunoaffinity column is constructed by covalently coupling anti-hCBP antibody to an activated chromatographic resin, such as CNBr-activated SEPHAROSE (Amersham Pharmacia Biotech). After the coupling, the resin is blocked and washed according to the manufacturer's instructions.

Media containing hCBP are passed over the immunoaffinity column, and the column is washed under conditions that allow the preferential absorbance of hCBP (e.g., high ionic strength buffers in the presence of detergent). The column is eluted under conditions that disrupt antibody/hCBP binding (e.g., a buffer of pH 2 to pH 3, or a high concentration of a chaotrope, such as urea or thiocyanate ion), and hCBP is collected.

XIV. Identification of Molecules Which Interact with hCBP hCBP, or biologically active fragments thereof, are labeled with $^{125}$I Bolton-Hunter reagent. (See, e.g., Bolton et al. (1973) Biochem. J. 133:529–539.) Candidate molecules previously arrayed in the wells of a multi-well plate are incubated with the labeled hCBP, washed, and any wells with labeled hCBP complex are assayed. Data obtained using different concentrations of hCBP are used to calculate values for the number, affinity, and association of hCBP with the candidate molecules. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI Auto Assembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W.R. (1990) Methods Enzymol. 183:63–98; and Smith, T. F. and M. S. Waterman (1981) Adv. Appl. Math. 2:482–489. | ESTs: fasta E value = 1.06E-6 Assembled ESTs: fasta Identity = 95% or greater and Match length = 200 bases or greater; fastx E value = 1.0E-8 or less Full Length sequences: fastx score = 100 or greater |

TABLE 1-continued

| Program | Description | Reference | Parameter Threshold |
|---|---|---|---|
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235:1501–1531; Sonnhammer, E. L. L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math: 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. A purified polypeptide comprising an amino acid sequence selected from the group consisting of:
   a) an amino acid sequence of SEQ ID NO:1, and
   b) a naturally-occurring amino acid sequence having at least 90% sequence identity to the sequence of SEQ ID NO:1, wherein said naturally-occurring amino acid sequence has calcium-binding activity.

2. An isolated polypeptide of claim 1, having a sequence of SEQ ID NO:1.

3. A method for producing a polypeptide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and
   b) recovering the polypeptide so expressed.

4. A composition comprising a polypeptide of claim 1 and a pharmaceutically acceptable excipient.

5. A composition of claim 4, wherein the polypeptide has the sequence of SEQ ID NO:1.

6. A method for screening a compound for effectiveness as an agonist of a polypeptide of claim 1, the method comprising:
   a) exposing a sample comprising a polypeptide of claim 1 to a compound, and
   b) identifying a compound that increases calcium binding activity.

7. A method for screening a compound for effectiveness as an antagonist of a polypeptide of claim 1, the method comprising:
   a) exposing a sample comprising a polypeptide of claim 1 to a compound, and
   b) identifying a compound that decreases calcium binding activity.

* * * * *